(12) United States Patent
Nelson

(10) Patent No.: US 8,162,910 B2
(45) Date of Patent: Apr. 24, 2012

(54) ABSORBENT ARTICLE HAVING COLORED REGIONS

(75) Inventor: Naomi Ruth Nelson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 970 days.

(21) Appl. No.: 12/116,529

(22) Filed: May 7, 2008

(65) Prior Publication Data

US 2009/0281513 A1 Nov. 12, 2009

(51) Int. Cl.
*A61F 13/15* (2006.01)

(52) U.S. Cl. ............ 604/385.01; 604/385.101; 604/378; 604/365; 604/368; 604/367; 604/366

(58) Field of Classification Search ............. 604/385.01, 604/385.101, 378, 365, 368, 367, 366
See application file for complete search history.

(56) References Cited

U.S. PATENT DOCUMENTS

| | | | |
|---|---|---|---|
| 5,897,541 A | 4/1999 | Uitenbroek et al. | |
| 6,811,239 B1 | 11/2004 | Salacz | |
| 7,402,157 B2 | 7/2008 | Christon et al. | |
| 2003/0135174 A1* | 7/2003 | Benecke et al. | 604/367 |
| 2006/0111684 A1 | 5/2006 | Berba et al. | |
| 2006/0264858 A1 | 11/2006 | Roe et al. | |
| 2007/0293834 A1 | 12/2007 | Miura et al. | |
| 2008/0132865 A1 | 6/2008 | Li et al. | |
| 2008/0294139 A1* | 11/2008 | Ecker et al. | 604/385.23 |

FOREIGN PATENT DOCUMENTS

EP 1 295 711 B1 4/2006

OTHER PUBLICATIONS

"Carefree Teens colored pantyliners, Personal Products, U.S.A., about 1990," Carefree Teens pantyliners for teenagers at the Museum of Menstruation and Women's Health (http://mum.org/crfrteen.htm).
"Multicolored Absorbent Articles: A Brief History," Jeffrey D. Lindsay and Beth A. Lange, Kimberly-Clark Corporation, Neenah, Wisconsin, Published in: IP.com's Prior Art Database, Oct. 10, 2003; Publication ID: IPCOM000019928D.
PCT International Search Report dated Aug. 17, 2009.

* cited by examiner

*Primary Examiner* — Jacqueline F. Stephens
(74) *Attorney, Agent, or Firm* — Amanda T. Barry; Gary J. Foose

(57) ABSTRACT

An absorbent article having colored regions. The absorbent article has at least three colored regions. The colored regions are spaced apart from one another. Each colored region has a major axis. The major axis of each colored region converges towards a common focal region on the longitudinal centerline of the absorbent article.

20 Claims, 9 Drawing Sheets

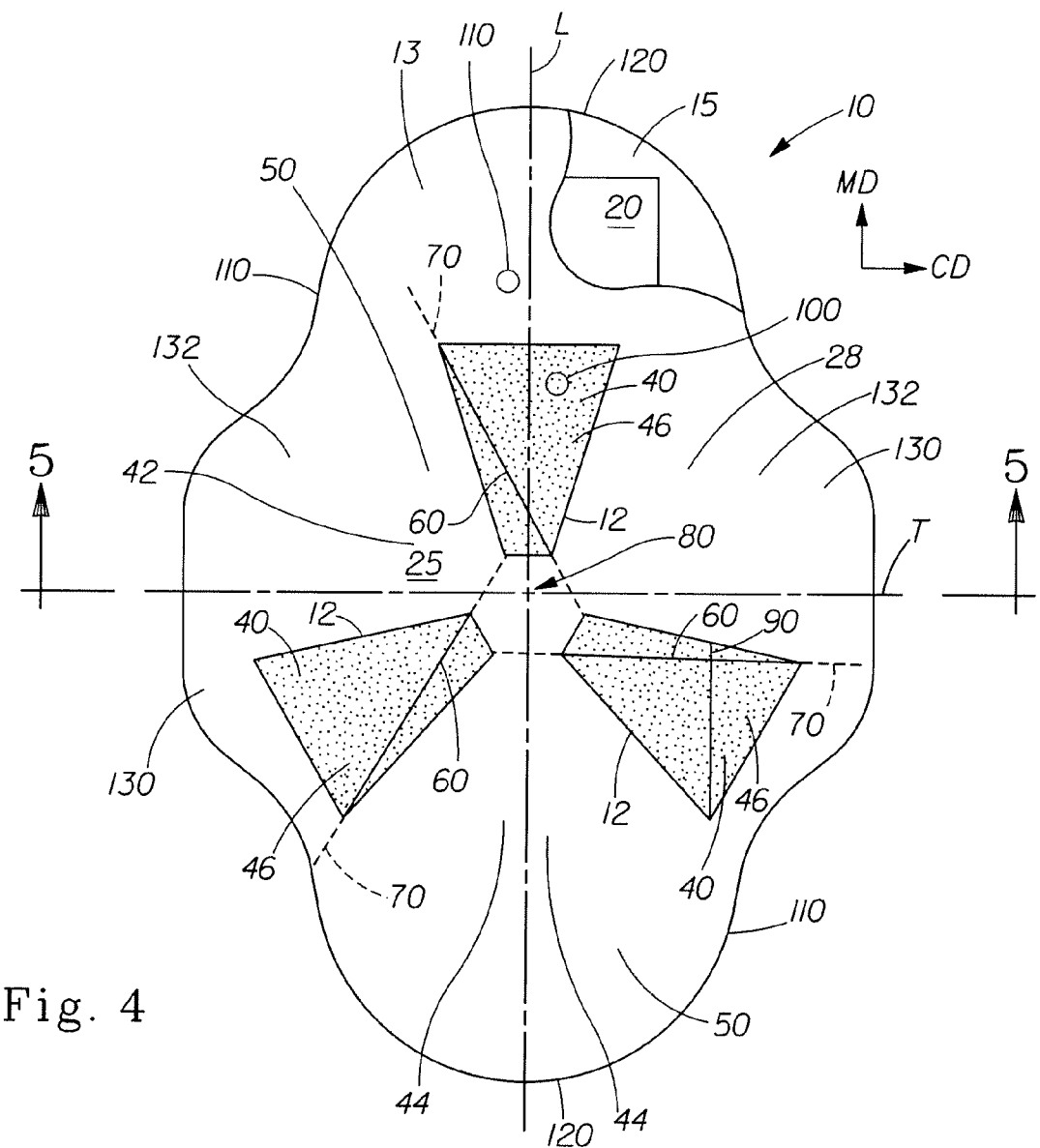
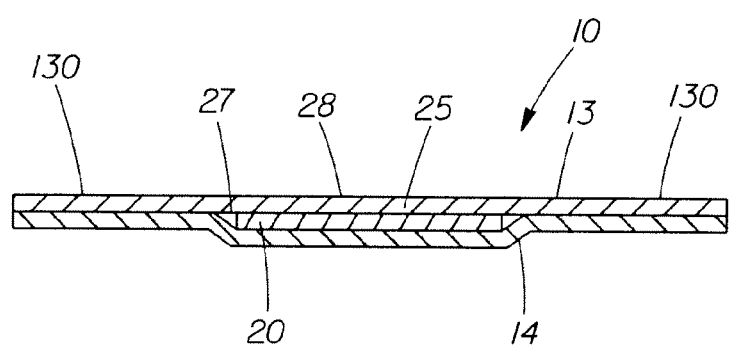
Fig. 4
Fig. 5

ABSORBENT ARTICLE HAVING COLORED REGIONS

FIELD OF THE INVENTION

The invention provides for an absorbent article having colored regions.

BACKGROUND OF THE INVENTION

Many consumers of absorbent articles associate the thickness of an absorbent article with the storage capacity of the absorbent article. Thus, designers of absorbent articles desire to create absorbent articles that are thick enough such that the consumers recognize that the absorbent article has enough storage capacity to protect the wearer of the absorbent article. Thicker absorbent articles tend to require more raw materials to form the absorbent article and the costs of raw material are a significant component of the cost to the supply side of the market. Thus, the cost to consumers of thicker absorbent articles can be more for some thicker absorbent articles than for some thinner absorbent articles.

From a technical perspective, improvements in material performance and the development of new materials have led to thinner absorbent articles that tend to be as effective, and in many cases, more effective, as previous generations of thicker absorbent articles. Nevertheless, some consumers may still believe that thicker absorbent articles might perform better than thinner absorbent articles. To serve these consumers, designers desire to create thicker absorbent articles while still keeping raw material costs low enough such that the absorbent articles are affordable to consumers. Increasing the thickness of absorbent articles may not be a desirable means to serve these consumers because the increase in the mass of raw materials in an absorbent article is likely to increase the cost of the absorbent article to the consumer. Thus, the consumer is left in an undesirable position of having to compromise her beliefs in how a particular absorbent article will perform with her desire to save money.

With these limitations in mind, there is a continuing unaddressed need for absorbent articles that appear to be thick enough to consumers so as to inspire confidence within the consumer that the absorbent article will deliver excellent performance without increasing the raw material costs of the absorbent article so as to make the absorbent article affordable to the consumer.

SUMMARY OF THE INVENTION

Disclosed is an absorbent article that can have a longitudinal centerline, a transverse centerline orthogonal to the longitudinal centerline, an upper surface, and a lower surface opposing the upper surface. The absorbent article can comprise a topsheet having a bottom surface and a viewing surface positioned opposite to the bottom surface, the viewing surface facing upwardly towards the upper surface of the absorbent article. The absorbent article can comprise at least three colored regions, the colored regions being viewable from the viewing surface of the topsheet, each of the colored regions having a periphery wherein none of the colored regions lie entirely within a periphery of another colored region. Each colored region can have a longest dimension and a major axis, the longest dimension defined by the maximum straight-line distance between two points on the periphery, the major axis extending between and beyond two points on the periphery separated by the longest dimension. The colored regions can be spaced apart from one another. The colored regions can have an aspect ratio greater than about one. The major axis of each of the colored regions converges towards a common focal region on the longitudinal centerline.

BRIEF DESCRIPTION OF THE DRAWINGS

FIG. 4 is a schematic of a plan view of an absorbent article having colored regions.
FIG. 5 is a schematic of a cross-sectional view of the absorbent article illustrated in FIG. 4 as marked in FIG. 4.

DETAILED DESCRIPTION OF THE INVENTION

"Absorbent articles", as referred to herein, include sanitary napkins, pantiliners, diapers, and adult incontinence pads/diapers that are worn in the crotch region of an undergarment. "Absorbent articles" further include tampons.

The term 'color', as referred to herein, can include any primary color, i.e., selected from the group consisting of red, green, and blue, and mixtures thereof. The term 'color', as referred to herein can include colors selected from the group consisting of white, black, red, blue, violet, orange, yellow, green, and indigo, and any declination thereof or mixture thereof.

The term 'disposable' is used herein to describe absorbent articles that are not intended to be launched or otherwise restored or reused as absorbent articles (i.e., they are intended to be discarded after a single use and possibly recycled, composted, or otherwise disposed of in a proper manner).

Non-limiting examples of panty liners and sanitary napkins which may be provided with colored regions that operate to create the perception of increased thickness include those manufactured by The Procter & Gamble Company of Cincinnati, Ohio as: ALWAYS® Pantiliners with DriWeave® manufactured according to U.S. Pat. Nos. 4,324,246; 4,463,045; and 6,004,893; ALWAYS® Ultrathin Slender Maxi with Wings manufactured according to U.S. Pat. Nos. 4,342,314, 4,463,045, 4,556,146, B1 4,589,876, 4,687,478, 4,950,264, 5,009,653, 5,267,992, and Re. 32,649; ALWAYS® Regular Maxi; ALWAYS® Ultra Maxi with Wings; ALWAYS® Maxi with Wings; ALWAYS® Ultra Long Maxi with Wings; ALWAYS® Long Super Maxi with Wings; and ALWAYS® Overnight Maxi with Wings.

Figure 1:
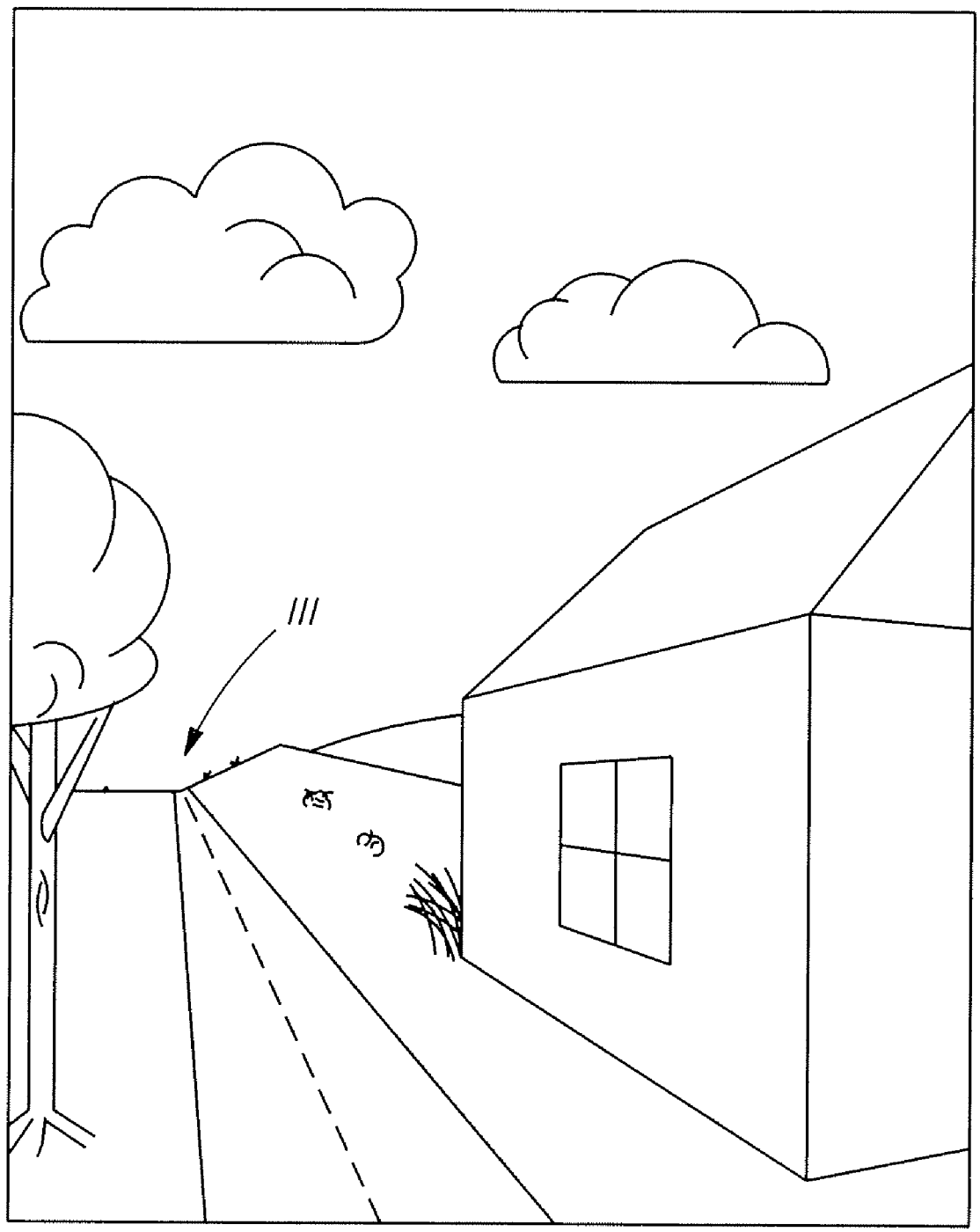
FIG. 1 is a drawing employing one-point perspective.

FIG. 1 illustrates an artistic rendering of a landscape in which an artistic technique known as one-point perspective is employed to impart three-dimensionality to a two-dimensional drawing. In one-point perspective, lines parallel with the line of sight of the observer converge towards the horizon towards a single vanishing point 111. In FIG. 1, the vanishing point 111 is just above the roadway where the roadway crests over the horizon. The foundation line of the house on the right that is parallel to the roadway and the roofline of the house parallel to the roadway are oriented such that projections thereof converge towards the vanishing point 111. Including perspective in the drawing in FIG. 1 can be thought of as providing depth to the drawing, making the foreground of the drawing, i.e. the house and tree, appear closer to the observer of the drawing than the background, i.e. the horizon and the location where the roadway crests over the horizon. One-point perspective is a powerful tool for creating the impression of depth, which essentially imparts visual "thickness", to two-dimensional artistic renderings.

Figure 2:
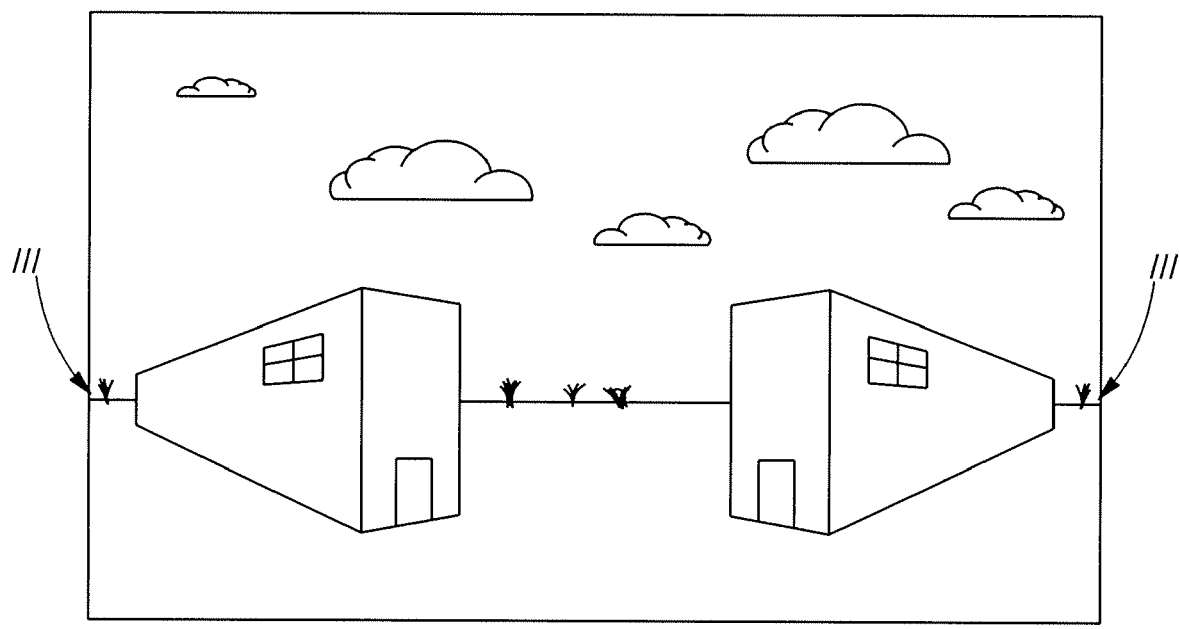
FIG. 2 is a drawing employing two-point perspective.

FIG. 2 is an artistic rendering of a landscape in which an artistic technique known as two-point perspective is employed to impart three-dimensionality to a two-dimensional drawing. In two-point perspective, lines parallel with the line of sight of the observer, i.e. the roof lines and foundation lines of sides of each building shown in FIG. 2, converge towards two vanishing points 111, depending on the location of the lines relative to the observer. In FIG. 2, the vanishing point 111 for the structure on the left, a corner of which is presented towards the observer, is off the left side of the drawing near the horizon. Similarly, the vanishing point 111 for the structure on the right, a corner of which is presented towards the observer, is near the right side edge of the drawing near the horizon.

Figure 3:
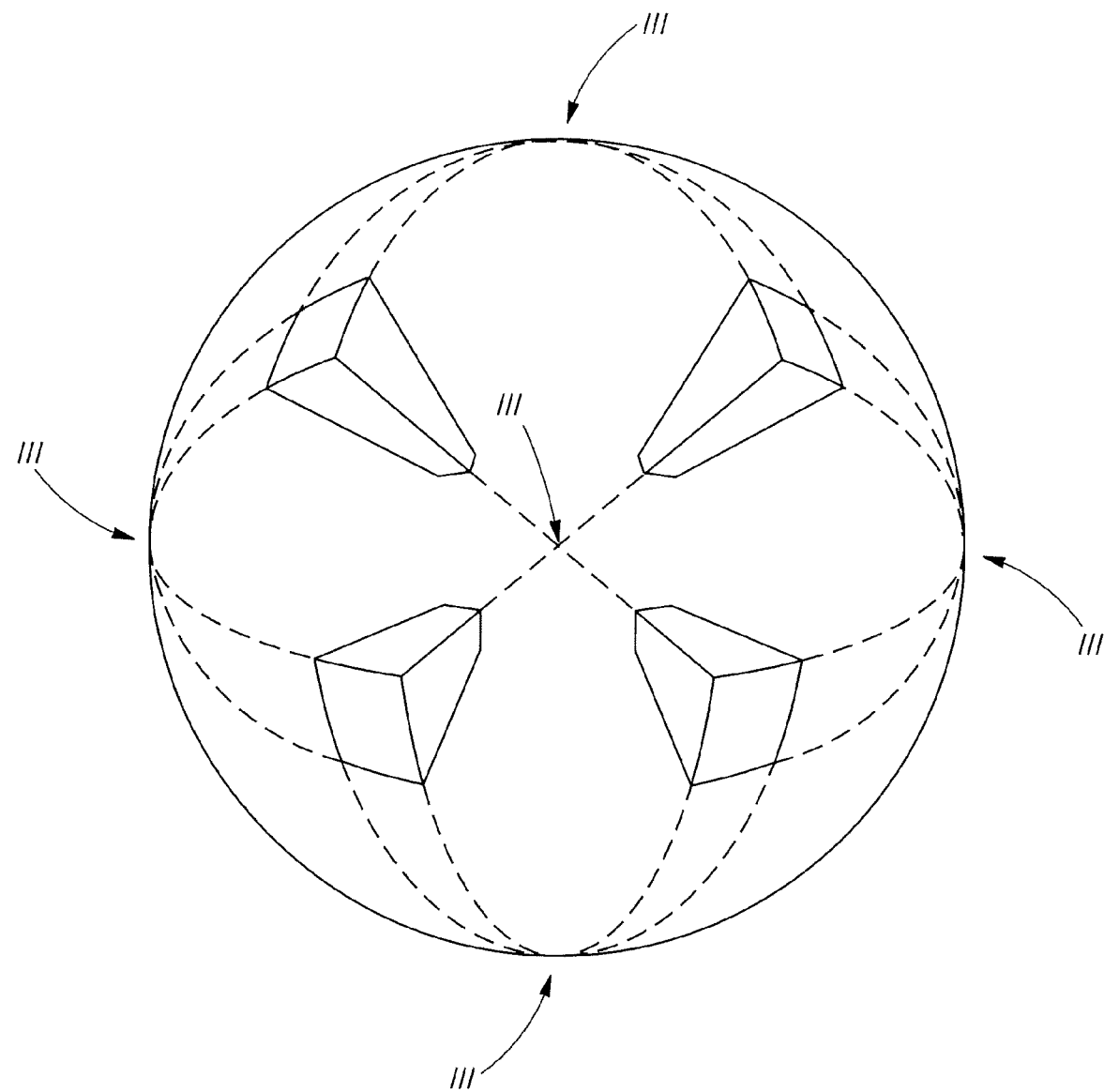
FIG. 3 is a drawing employing five-point perspective.

FIG. 3 is a drawing employing five-point curvilinear perspective to impart three-dimensionality to a two dimensional drawing. The five vanishing points 111 in FIG. 3 are a point at the top of the circle, a point at the bottom of the circle, a point on the left side of the circle, a point at the right side of the circle, and a point at the center of the circle. Other numbers of vanishing points 111, including three, four, and six can be used, depending on the desired perspective the artist wishes to create.

One common feature that can be recognized in FIGS. 1, 2, and 3 is that the perception of depth in the drawings is strong for objects that are illustrated as having a long axis and a short axis with the long axis generally aligned in a direction towards a vanishing point. For example, in FIG. 1 the appearance of depth for the roadway and side of the house are strong. In FIG. 2, the appearance of depth for the long sides of the buildings is strong. In FIG. 3, the tall rectangular parallelepipeds appear to radiate outwardly from the vanishing point at the center.

The objective of an artist who uses perspective drawing is to impart depth to a two-dimensional drawing. Like an artist working with a two-dimensional canvas upon which to draw or paint, designers of absorbent articles are working with a structure that is generally planar. That is, for typical absorbent articles, the extent of the absorbent article in plane is substantially greater than the thickness of the absorbent article. Without being bound by theory, it is believed that employing colored regions having shapes like those in FIGS. 1, 2, and 3, the shapes being associated with fundamental principles of art and perspective, can be used to create absorbent articles that give the visual impression that the absorbent article is thick enough to deliver excellent performance. The visual impression of thickness is possibly due to the perception of depth generated by the shapes employed. By employing such colored regions, designers can reduce the amount of raw material used yet can still create an absorbent article that looks thick, all the while keeping the cost to the consumer as low as possible. Such a proposition is attractive given that there are wide variety of relatively inexpensive advanced materials that can be employed in absorbent articles to allow the articles to absorb large volumes of fluid yet still allow absorbent articles and materials thereof to be relatively thin compared to previous generations of absorbent articles. Advanced materials, including high internal phase emulsion foams, foamed absorbent gelling material, particulate absorbent gelling materials; and chitosan, can absorb tremendous quantities of fluid in small volumes of absorbent material. With such materials, designers can use low basis weight materials and low volume materials resulting in generally thin absorbent articles that can absorb a large volume of fluid.

FIG. 4 illustrates an absorbent article 10 having a longitudinal centerline L, a transverse centerline T orthogonal to the longitudinal centerline L. The absorbent article 10 has an upper surface 13, a lower surface, two spaced apart longitudinal side edges 110, and two spaced apart transverse end edges 120. The upper surface 13 of the absorbent article 10 can be fluid pervious. The upper surface 13 of the absorbent article 10 can be the body facing surface of the absorbent article such that that when worn, the upper surface 13 is oriented towards the wearer's body. The absorbent article 10 has a machine direction MD and a cross-machine direction CD. The absorbent article 10 can have a pair of flaps 130 sized, dimensioned, and positioned for folding around and securing the absorbent article to the wearer's undergarment. The flaps 130 can be associated with the main body portion 42 at a juncture 132, with one flap 130 extending laterally outward from each longitudinal side edge 110. The main body portion 42 has a main body portion area 44 which is the area of the main body portion 42 in the MD-CD plane.

The absorbent article 10 comprises a topsheet 25 having a bottom surface and a viewing surface 28 positioned opposite to the bottom surface. The viewing surface 28 faces upwardly towards the upper surface 13 of the absorbent article 10.

The absorbent article 10 further comprises at least three colored regions 40. The colored regions 40 are viewable from the viewing surface 28 of the topsheet 25. Each colored region 40 has a periphery 12 and can be arranged such that none of the colored regions 40 lie entirely within the periphery 12 of another colored region 40.

Each colored region 40 has a longest dimension 60 and a major axis 70. The longest dimension 60 is defined by the maximum straight-line distance between two points on the periphery 12 of a colored region 40. The major axis 70 extends between and beyond two points on the periphery 12 separated by the longest dimension 60. There need not be a unique longest dimension 60 and major axis 70 for each colored region 40. That is, a colored region may have two or more longest dimensions 60 that are equal to one another and corresponding major axes 70. Each of the colored regions 40 can have an aspect ratio greater than about one. The aspect ratio of a colored region 40 is the ratio between the longest dimension 60 and the maximum width 90 of the colored region 40. The width 90 of a colored region 40 is measured orthogonal to the major axis 70 of the colored region. The width 90 of a colored region 40 can vary along the major axis 70 of the colored region 40.

The major axis 70 of each of the colored regions 40 can converge towards a common focal region 80 on the longitudinal centerline L. The focal region 80 is like the vanishing point 111 in the artistic renderings shown in FIGS. 1-3 and is a location from which the visual impression of depth emanates from or descends into. The focal region 80 can be a general area or a single point yet still be a location from which depth of the absorbent article 10 is apparent. The focal region 80 can be a region that is symmetrical about the longitudinal centerline L. The focal region 80 can have a focal region area 82 that is the area of the focal region in the MD-CD plane. The focal region area 82 can be less than about 3% of the main body portion area 44. The focal region area 82 can be less than about 1% of the main body portion area 44. The focal region area 82 can be less than about 8% of the main body portion area 44. The focal region 80 can be at the intersection of the longitudinal centerline L and the transverse centerline T.

The focal region 80 can be the general area bounded by intersections of the major axes 70 of the colored regions 40. The focal region 80 can be a single point if the major axes 70 of each of the colored regions 40 intersect one another at a single point. The focal region 80 can be either the region that appears to be closest to the viewer or the region that appears to be furthest away from the viewer, depending on how the colored regions 40 are arranged and how the viewer's brain interprets the image. The focal region 80 can be the general region that appears to be most deeply embedded in the absorbent article 10. The focal region 80 can be the general region that appears to be the thickest portion of the absorbent article. The focal region 80 can be identified by projecting the major axis 70 of each colored region towards the longitudinal centerline L and identifying each location at which two major axes 70 intersect, the points of intersection being the general boundary of the focal region 80.

The colored regions 40 arranged as described herein are believed to operate to create the visual impression that the absorbent article is thick enough to deliver excellent performance. Without being bound by theory, it is believed that a generally thin and flat absorbent article can be made to have a visual impression of a relatively thick absorbent article by employing colored regions 40 having an aspect ratio greater than about one and having major axes 70 deployed about a focal region. For instance, the focal region 80 in FIG. 4 can appear to the observer to be above the MD-CD plane of the absorbent article. By creating such a visual impression, designers of absorbent articles may be able to provide to consumers absorbent articles that use less material that will be less expensive for the consumer to purchase that might appear to be thick. Designers can provide for high absorbent capacity by employing advanced absorbent materials that are thin yet still are able to absorb a large quantity of fluid. Thus, thinner absorbent articles 10, which are believed to be more comfortable to wearers and might be less expensive, can be provided to consumers and the consumer will still be able to perceive the high absorbent capacity of the absorbent article 10 by the apparent thickness of the absorbent article 10.

The shapes of the colored regions 40 in FIG. 4 are similar to those in FIGS. 1-3. For instance the colored regions 40 in FIG. 4 are similar to the shape of the side of the house aligned with the roadway illustrated in FIG. 1, the sides of the buildings in FIG. 2, and the long sides of the rectangular parallelepipeds in FIG. 3. Without being bound by theory, it is thought that shapes similar to those illustrated in FIGS. 1-3 disposed about a focal region 80 being viewable from the viewing surface 28 of the absorbent article 10 can operate to create the visual impression of depth, which can make the absorbent article 10 appear to be thick as compared to an absorbent article 10 that is not provided with such colored regions 40.

The absorbent article 10 can comprise an absorbent core 20. The absorbent core 20 can be positioned between the topsheet 25 and the backsheet 15 and can be in facing relationship with the topsheet 25. The absorbent article 10 can have a background region 50. The colored regions 40 and the background region 50 are viewable from the viewing surface 28 of the topsheet 25.

The color of a colored region 40 and the background region 50 can be measured by the reflectance spectrophotometer according to the colors' L*, a*, and b* values. The L*, a*, and b* values can be measured from the viewing surface 28 of the topsheet 25 inboard of the periphery 12 of the absorbent article 10. The color differences between the colored region 40 and the background region 50 can be measured at a first location 100 and a second location 110 on the viewing surface 28 of the topsheet 25 inboard of the periphery 12 of the absorbent article 10. The first location 100 and second location 110 can reside fully within the maximum lateral extent of the absorbent core 20 in the MD-CD plane. For example, the first location 100 can be within a colored region 40 and the second location 110 can be measured within the background region 50 of the absorbent article 10.

The background region 50 can be the color white which is further defined as those colors having an L* value of at least 90, an a* value equal to 0±2, and a b* value equal to 0±2. The color of the background region 50 can be dictated by the constituent material without any additional process performed thereon to provide the background region 50 with a color different from the constituent material.

The colored regions 40 can be spaced apart from one another. That is, the colored regions 40 can be arranged such that the periphery 12 of one colored region 40 does not overlap with the periphery 12 of another colored region 40.

The colored regions 40 can be designed such that the width 90 of each colored region generally decreases with decreasing distance from the focal region 80.

FIG. 5 is a schematic of a cross section as marked in FIG. 4. As shown in FIG. 5, the absorbent article 10 has a lower surface 14, which opposes the upper surface 13. The bottom surface 27 of the topsheet 25, which opposes the viewing surface 28 of the topsheet 25, is also shown.

Figure 6:
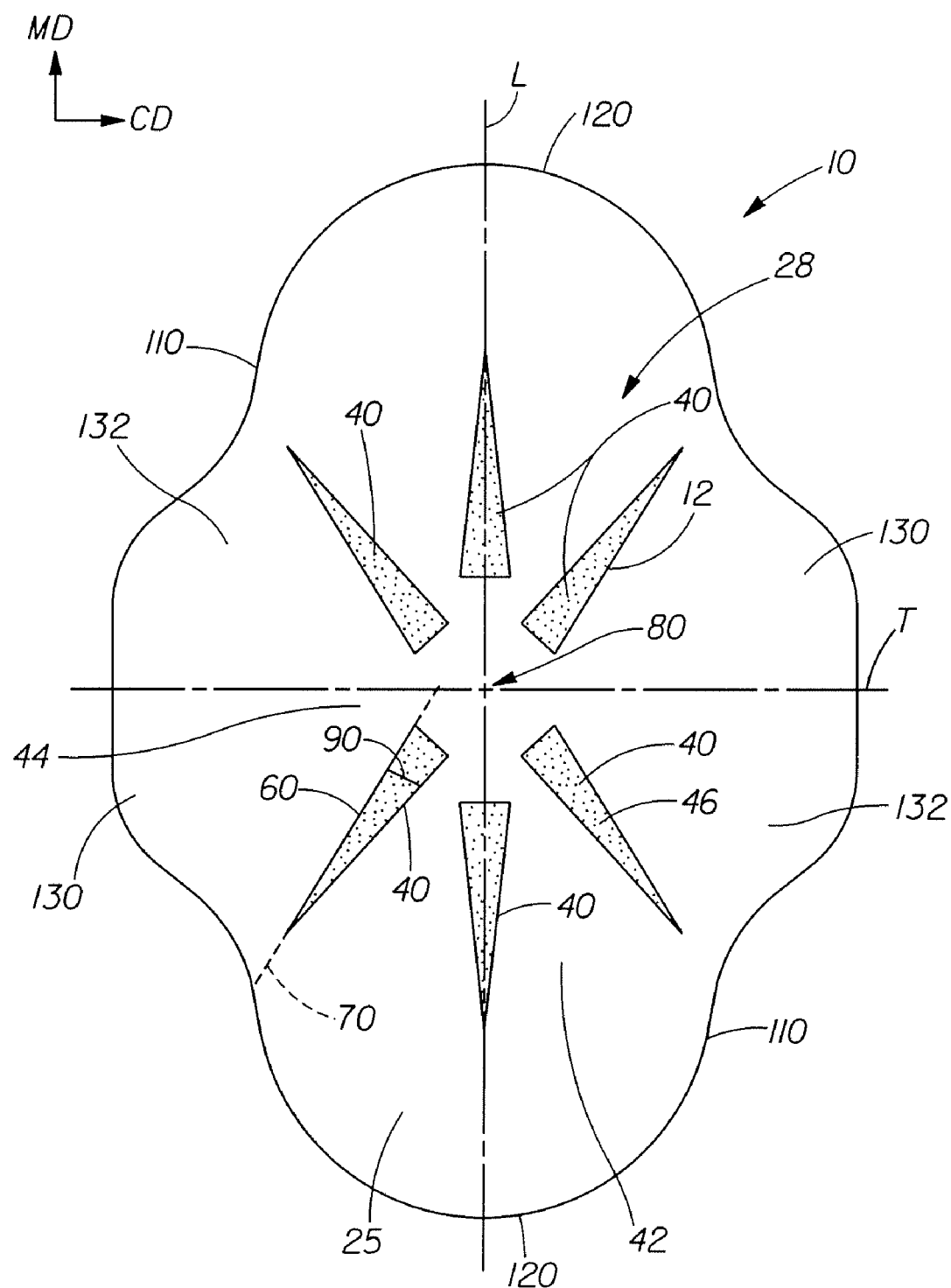
FIG. 6 a schematic of a plan view of an absorbent article having colored regions.

FIG. 6 is a schematic of an embodiment in which the width 90 of each colored region generally increases with decreasing distance from the focal region 80. In this arrangement, it is believed that by having the major axis 70 of each colored region 40 convergent upon one anther in a common focal region 80 the absorbent article 10 appears to be thicker than an absorbent article having the same thickness but not having the colored regions 40. The colored regions 40 in FIG. 6 are shaped like the roadway in FIG. 1 and the sides of the buildings in FIG. 2. By having such shape, it is postulated that the viewer's brain interprets the shapes of the colored regions 40 as indicating and/or adding depth to the view.

Depending on the desired optical effect, the colored region area 46 of each colored region 40 can be more than about 1% of the main body portion area 44. The colored region area 46 is the area of a colored region 40 in the MD-CD plane. For absorbent articles having flaps 130 for wrapping around and securing the absorbent article 10 to the wearer's undergarment, the main body portion 42 does not include the flaps 130. Similarly, the main body portion area 44 does not include the area of the flaps in the MD-CD plane.

The colored regions 40 can be arranged in a variety of configurations. For instance, there can be at least two of the colored regions 40 can disposed on opposing sides of a line parallel to the transverse centerline T and at least two colored regions can be disposed on opposing sides of the longitudinal centerline L, as shown in FIGS. 4 and 6, for example. By spacing apart the colored regions 40 in such a manner, it is believed that the optical effect of the colored regions 40 in creating depth is stronger.

The color differences can be calculated using the L*, a*, and b* values by the formula $\Delta E=[(L^*_X-L^*_Y)^2+(a^*_X-a^*_Y)^2+(b^*_X-b^*_Y)^2]^{1/2}$. Herein, the 'X' in the equation may represent the first location 100 or the second location 110. Y may represent the first location 100 or the second location 110. X and Y should not be the same two locations of measurement at the same time. In other words, X≠Y. For the calculation herein, 'X' and 'Y' values should not stem from the same measured location on the viewing surface 28.

The difference in color (ΔE*) between the colored region 40 and the background region 50 can be at least about 3.5. The difference in color between the colored region 40 and the background region 50 can be at least about 6.

In one embodiment herein, the colored regions 40 can be on an insert positioned between the topsheet 25 and the absorbent core 20. In another embodiment, the colored regions 40 can form a part of the topsheet 25. In another embodiment, the colored regions 40 can form part of the bottom surface 27 of topsheet 25. In another embodiment, the colored regions 40 can form a part of the absorbent core 20 whereby the colored regions 40 are viewable from the viewing surface 28 of the topsheet 25. Alternatively, the colored regions 40 may be on an insert or a multi-layered insert positioned beneath the topsheet 25. The insert can be between the topsheet 25 and absorbent core 20 and can be absorbent or nonabsorbent.

Any topsheet material that allows the colored regions 40 to be readily seen from the viewing surface 28 of the topsheet 25 is suitable. For example, formed film material, nonwovens, or combinations thereof are suitable.

Figure 7:
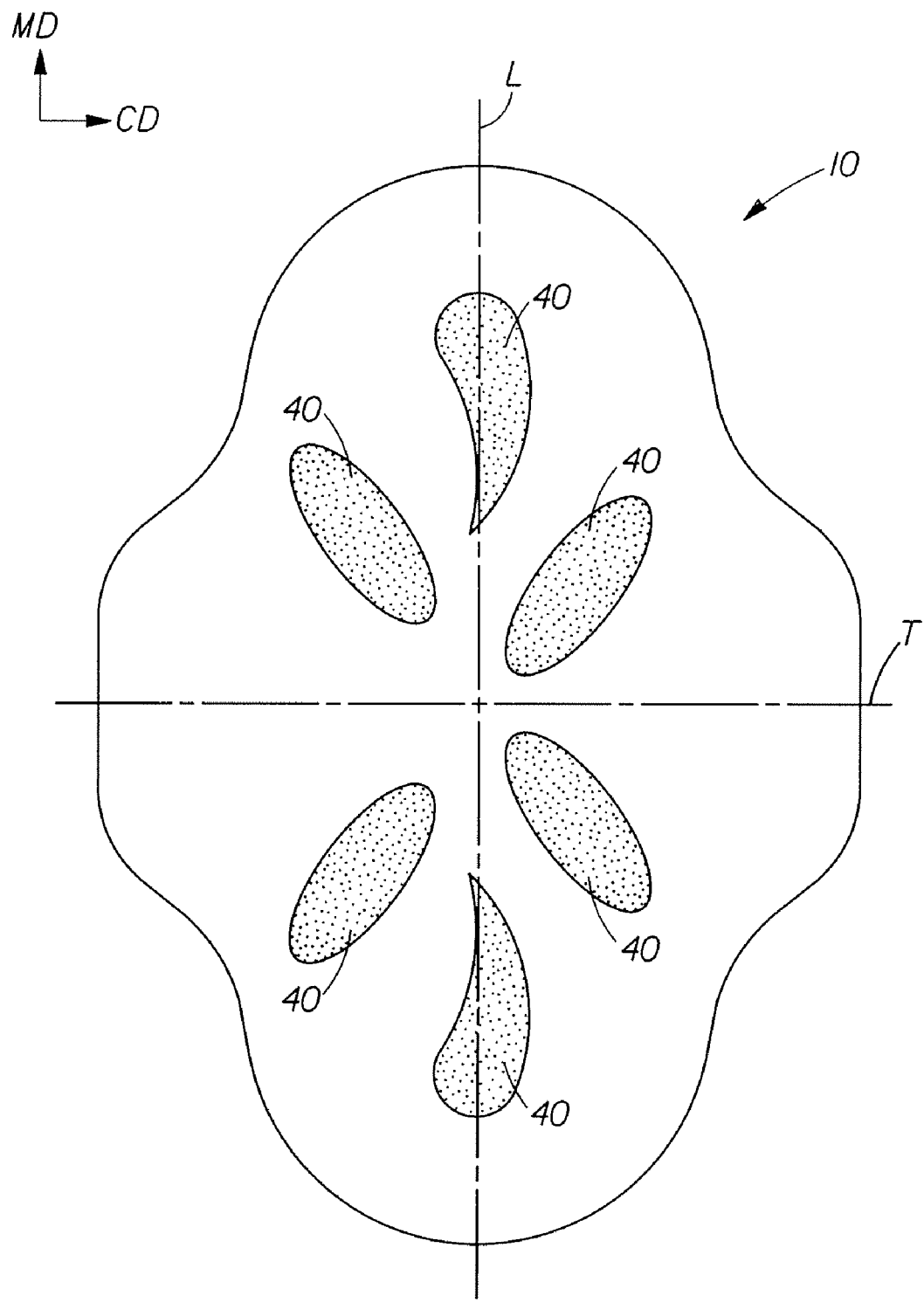
FIG. 7 is a schematic of a plan view of an absorbent article having colored regions.
Figure 8:
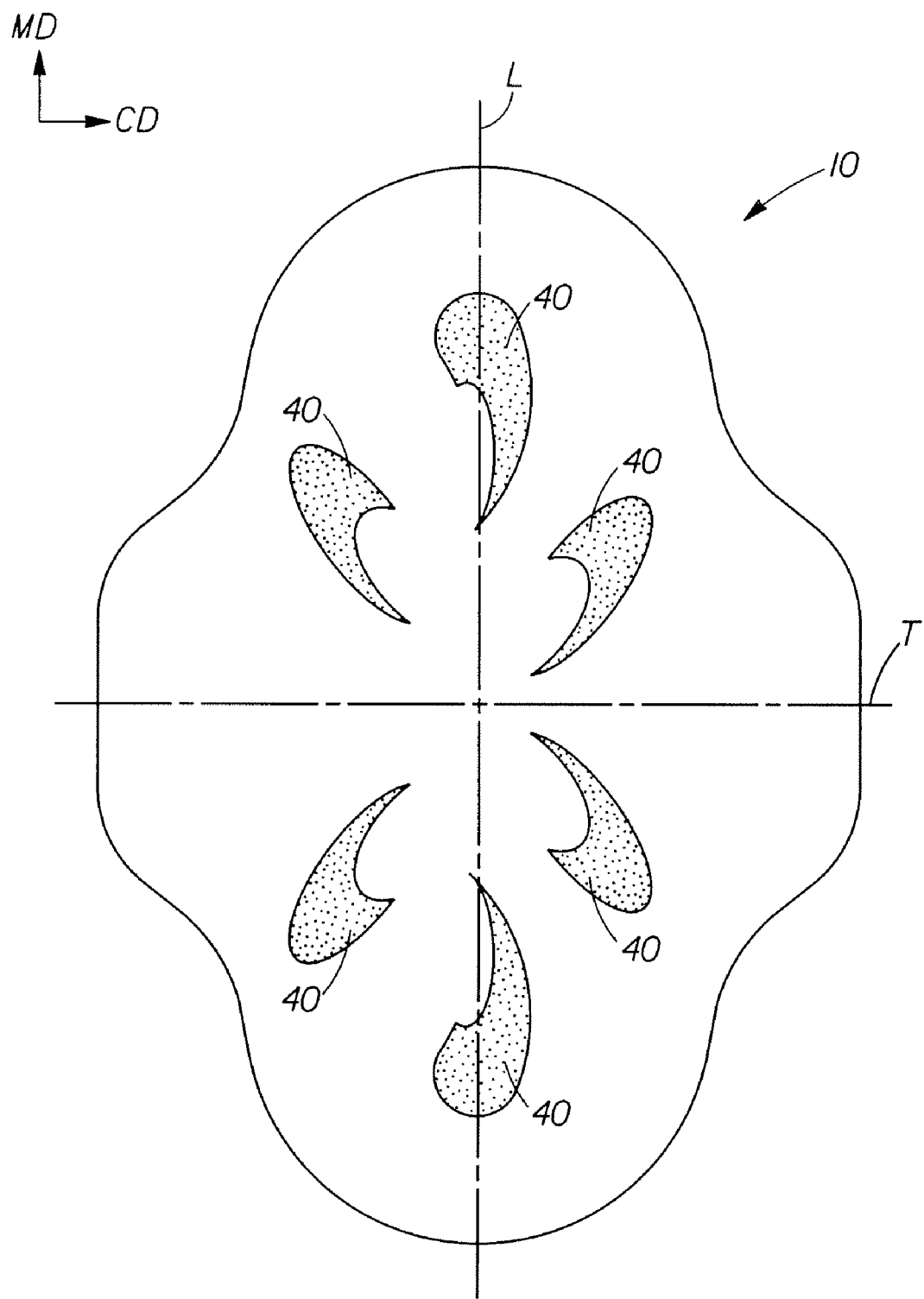
FIG. 8 is a schematic of a plan view of an absorbent article having colored regions.

FIGS. 7 and 8 illustrate embodiments having colored regions 40 having a variety of shapes. In each of these embodiments, the colored regions 40 are believed to be shaped and arranged such that the absorbent article 10 appears to be thicker than an absorbent article 10 not having such colored regions 40. The colored regions 40 in FIGS. 7 and 8 are arranged in a manner similar to those in FIG. 3 in that the major axes 70 of the colored regions 40, which are elongated shapes, converge upon one another in a common region near the intersection of the longitudinal centerline L and the transverse centerline T. The sides of the rectangular parallelepipeds in FIG. 3 are also elongated shapes, the long axes of which tend to be oriented about a common region near the center focal point 111. Even with the gently contoured peripheral shapes of the colored regions 40 in FIGS. 7 and 8, the effect on thickness and/or depth perception can be the same.

Figure 9:
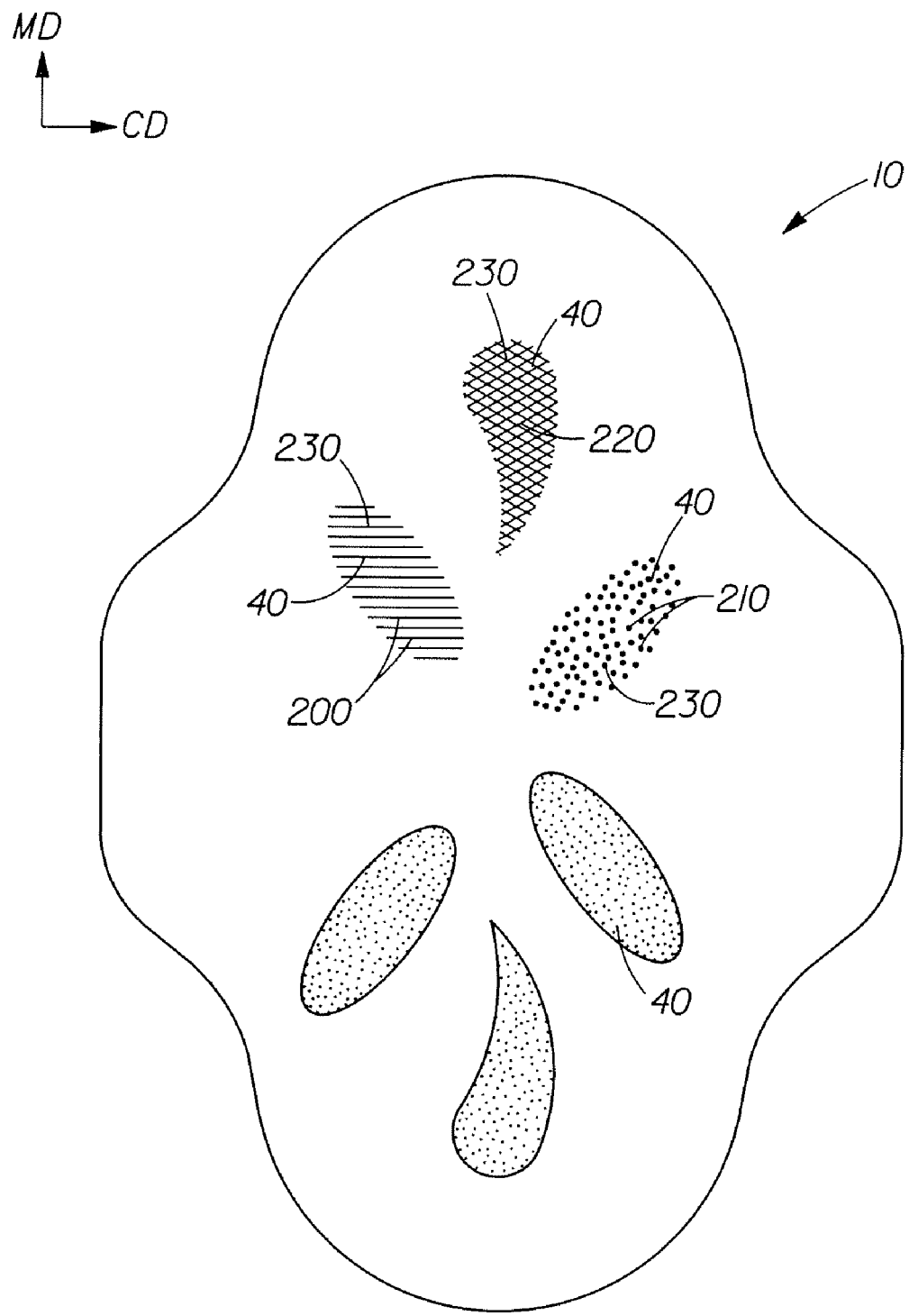
FIG. 9 is a schematic of a plan view of an absorbent article illustrating alternative embodiments of colored regions.

Color can be provided to the colored regions 40 by any of the approaches known in the graphic arts for providing areas that are perceived by the viewer to have color. For instance, a colored region 40 can comprise a plurality of closely spaced lines 200, as shown in FIG. 9, the lines being curved, straight, or a combination of curved and straight segments. Another approach for creating an area that is perceived to have color is to form a colored region 40 by a plurality of closely spaced dots 210, such as a stippling pattern. Another approach for creating an area that is perceived to have color is to form a colored region 40 by cross-hatching 220 that is fine enough to give the impression of color. In effect, a plurality of closely spaced graphic elements 230, including, but not limited to, those selected from the group consisting of lines 200, dots 210, cross-hatching 220, and combinations thereof can yield a colored region 40 that is perceived by the viewer to have color.

Figure 10:
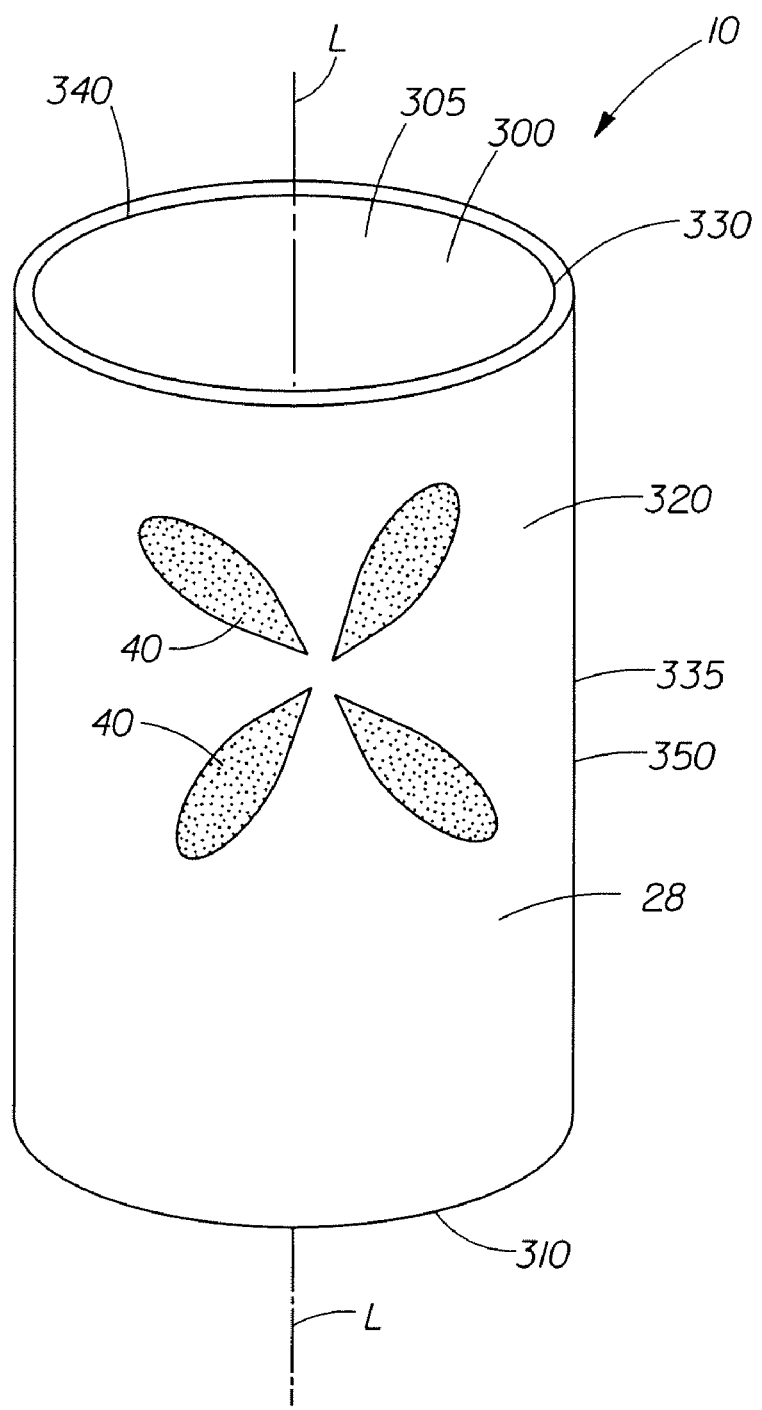
FIG. 10 is a schematic of a tampon having colored regions.

In an alternative embodiment, an example of which is shown in FIG. 10, the absorbent article 10 can comprise a compressed absorbent member 300 having an insertion end 305, a withdrawal end 310, a longitudinal axis L, and a circumferential surface 330 about the longitudinal axis L. The absorbent article 10 comprises an exterior surface 335. The exterior facing surface 335 can be the viewing surface 28. The exterior surface 335 can be the surface of the compressed absorbent member 300 oriented away from the longitudinal axis L.

The absorbent article 10 can further comprise at least three colored regions 40. The colored regions 40 are viewable from the viewing surface 28 of the absorbent article 10. The embodiment shown in FIG. 10 is commonly referred to in the art as a tampon. The colored regions 40 can be part of the compressed absorbent member 300.

The absorbent article can optionally further comprise an overwrap 320 substantially covering the circumferential surface 330 of the compressed absorbent member 300, as shown in FIG. 10. The overwrap 320, if present, has an inner facing surface 340 and an outer facing surface 350 opposing the inner facing surface 340. The inner facing surface 340 is oriented towards the absorbent member 300 and the outer facing surface 350 can be the viewing surface 28. The colored regions 40 can be part of either the outer facing surface 350 or inner facing surface 340 of the overwrap 320. The colored regions 40 can be part of the overwrap 320. The colored regions 40 can be part of an insert (that can be absorbent or non-absorbent) that is between the overwrap 320 and the compressed absorbent member 300.

The compressed absorbent 300 can be any material suitable for use in absorbent tampons including, but not limited to, cellulose, foam, and polyolefin nonwoven materials. The overwrap can be, for example, a polyolefin nonwoven or woven web, gauze, or like material.

The difference in color between a colored region 40 and a portion of the absorbent article 10 outside of the colored region 40, or in the background region 50, can be determined by visual inspection or an analytical method such as described below. The analytical method described below may be practical for colored regions 40 that comprise solid colors and embodiments comprising closely spaced graphic elements 230 for which one skilled in the art can adapt the analytical method. For colored regions 40 comprising a plurality of closely spaced graphic elements 230, the visual impression of a human observer having normal color vision observing the absorbent article 10 having colored regions 40 under a 100 watt incandescent light bulb from a distance of 30 cm can be used to determine if the absorbent article has colored regions 40.

Analytical Methodology—Hunter Color

The color scale values, that can be used to define the darkness/lightness of the materials of the absorbent articles according to the present invention, can be the widely accepted CIE LAB scale. Measurements can be made with a Hunter Color reflectance meter. A complete technical description of the system can be found in an article by R. S. Hunter, 'photoelectric color difference Meter', Journal of the Optical Society of America, Vol. 48, pp. 985-95, 1958. Devices that are specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher the value is, the lighter the color is since a lighter colored material reflects more light. In particular, in the Hunter Color system the "L" scale contains 100 equal units of division. Absolute black is at the bottom of the scale (L=0) and absolute white is at the top of the scale (L=100). Thus in measuring Hunter Color values of the materials used in the absorbent articles according to the present invention, the lower the "L" scale value, the darker the material. The absorbent articles herein, and hence the materials of which the absorbent articles are made of, can be of any color provided that the L Hunter value defined herein is met.

Colors can be measured according to an internationally recognized 3D solid diagram of colors where all colors that are perceived by the human eye are converted into a numerical code. The CIE LAB system is similar to Hunter L, a, and b and is based on three dimensions, specifically L*, a*, and b*.

When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue).

A color may be identified by a unique ΔE value (i.e., different in color from some standard or reference), which is mathematically expressed by the equation:

$$\Delta E^* = [(L^*_X - L^*_Y)^2 + (a^*_X - a^*_Y)^2 + (b^*_X - b^*_Y)^2]^{1/2}$$

'X' represents the standard or reference sample. The standard or reference sample can be a 'white' sample or a 'colored' sample, e.g., one colored shade may be compared to another colored shade. For example the background region 50 can be the standard reference sample 'X' and the colored region 40 can be considered as the variant 'Y'.

It is to be understood that the tristimulus color values and ΔE* considered herein can be those measured on the materials of interest (e.g., the colored regions 40 and background region 50 visible from observation of the viewing surface 28).

The Hunter color meter quantitatively determines the amount (percent) of incident light reflected from a sample onto a detector. The instrument is also capable of analyzing the spectral content of the reflected light (e.g., how much green is in the samples). The Hunter color meter is configured to yield 3 values (L*, a*, b* and ΔE* which is total color). The L* value is the percent of the incident (source) light that is reflected off a target sample and onto the detector. A shiny white sample will yield an L* value near 100 while a dull black sample will yield an L* value of about 0. The a* and b* value contains spectral information for the sample. Positive a* value indicates the amount of green in the sample.

Testing can be conducted using a Lab Scan XE 45/0 geometry instrument to measure the colored regions 40 and the background region 50. The Hunter Color in CIE lab scale 2° C. can be measured. The diameter of the port is to be selected based on the area upon which color measurement is to be made, with the size of the port being the largest port available that provides for an area view that is smaller than the area upon which color measurement is made. A 0.2 inch diameter port can be used. A 0.7 inch diameter port can be used having a 0.5 inch area view. The instrument is to be calibrated using standard white and black tiles supplied by the instrument manufacturer prior to use for measurements.

Color Zone Measurement for Pad Topsheet Appearance

For measuring the L*, a*, and b* values for the invention herein, a standard, industry-recognized procedure is used. The topsheet color is measured using a reflectance spectrophotometer in accordance with method ASTM E 1164-94, "Standard Practice for Obtaining Spectrophotometric Data for Object-Color Evaluation". This standard method is followed but specific instrument settings and sampling procedure are given here for clarity. Sample color can be reported in terms of the CE 1976 color coordinate standard as specified in ASTM E 1164-94 and ASTM D2264-93, section 6.2. This consists of three values; L* which measures sample "lightness", a* which measures redness or greenness, and b* which measures yellowness or blueness.

Apparatus

Reflectance Spectrophotometer . . . 45°/0° Hunter Labscan XE, or equivalent
  HunterLab Headquarters, 11491 Sunset Hills Road, Reston Va. 20190-5280 Tel: 703-471-6870 Fax: 703-471-4237
  http://www.hunterlab.com.
Standard plate . . . Sandard Hunter White Tile Source: Hunter Color.

Equipment Preparation
1. Assure that the Spectrophotometer is configured as follows:
  Illumination . . . Type C
  Standard Observer . . . 2°
  Geometry . . . 45/0° Measurement angle
  Port Diameter . . . select port diameter based upon the area upon which color measurement is to be made
  Viewing area . . . to be selected based upon the area upon which color measurement is to be made
  UV Filter: Nominal
2. Calibrate the spectrophotometer using standard black and white tiles supplied with the instrument according to manufacturer's instructions before beginning any testing.

Sample Preparation
1. Unwrap, unfolded and lay the product or pad samples flat without touching or altering the color of the body facing surface.
2. Areas on the viewing surface of the product should be selected for measurement and must include the following:
  The background region of the viewing surface.
  The colored region of the viewing surface.
  Any other portions of the viewing surface having a visibly or measurably different color from the colored region. Embossed channels and folds should not be included in zones of measurement as they may skew the proper results. Measurements should not be made overlapping the border of two shaded portions.

Test Procedure
1. Operate the Hunter Colorimeter according to the instrument manufacturer's instructions.
2. The absorbent article should be measured laying flat over the aperture on the instrument. A white tile should be placed behind the pad.
3. The absorbent article should be placed with its long direction perpendicular to the instrument.
4. Measure the same zones selected above for at least 3 replicate samples.

Calculation Reporting
1. Ensure that the reported results are really CE L*,a*,b*.
2. Record the L*,a*,b* values to the nearest 0.1 units.
3. Take the average L*, a*, b* for each zone measured.
4. Calculate ΔE* between a colored region and the background.

Human Sensitivity to Light

The human sensitivity threshold for the lightness of a dark green color is a ΔE* of about 1.0. For a dark green color, if only the a* and b* change, human sensitivity is a ΔE* of 2.4. In the context of an absorbent article herein (e.g., a sanitary napkin) it is highly likely that many people would not see a color difference if the ΔE* is less than 2. This sensitivity is described in the following reference: "The Measurement of Appearance", by Hunter and Harold, 2nd edition, 1987, (ISBN 0-471-83006-2).

Chapter 4 of Hunter's book describes human color sensing and chapter 9 is about color scales. By making side-by side comparison, humans can differentiate up to 5 to 10 million different colors. In the 1940s, a researcher named MacAdam did human chromaticity discrimination experiments. He found the thresholds of sensitivity and showed these depend on the color. Later work by Brown and MacAdam came up with a logarithmic lightness dimension scale for human sensitivity to go with the earlier color scale. A ΔE≧3.5 can provide sufficient definition of the colored regions to provide for the effect of the appearance of depth. However, where the ΔE is as small as about 1 and still operates to provide a perception of depth between the shades, this ΔE is also contemplated and included herein.

As has been noted previously, the difference in color between colored region 40 and a background region 50 can be at least 3.5. The difference in color between colored region 40 and a background region 50 can be at least 6.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline, a transverse centerline orthogonal to said longitudinal centerline, an upper surface, and a lower surface opposing said upper surface, said absorbent article comprising;
   a topsheet having a bottom surface and a viewing surface positioned opposite to the bottom surface, said viewing surface facing upwardly towards said upper surface of said absorbent article; and
   at least three colored regions, said colored regions being viewable from said viewing surface of said topsheet, each said colored region having a periphery wherein none of said colored regions lie entirely within a periphery of another colored region;
   wherein each said colored region has a longest dimension and a major axis, said longest dimension defined by the maximum straight-line distance between two points on said periphery, said major axis extending between and beyond two points on said periphery separated by said longest dimension, wherein said colored regions are spaced apart from one another and are provided in a region fully within the maximum lateral extent of the absorbent core;
   wherein each said colored region has an aspect ratio greater than about one;
   said major axis of each said colored region converging towards a common focal region on said longitudinal centerline, said major axis of each of said colored regions being oriented about said focal region and extending toward an edge of said absorbent article.

2. The absorbent article according to claim 1, wherein each said colored region has a width measured orthogonal to said major axis of said colored region, wherein said width generally decreases with decreasing distance from said focal region.

3. The absorbent article according to claim 1, wherein each said colored region has a width measured orthogonal to said major axis of said colored region, wherein said width generally increases with decreasing distance from said focal region.

4. The absorbent article according to claim 1, wherein said absorbent article has two spaced apart longitudinal side edges, and two spaced apart transverse end edges, wherein said absorbent article has a main body portion defined by said two spaced apart longitudinal side edges and said two spaced apart transverse end edges, wherein said main body portion has a main body portion area bounded by said longitudinal side edges and said transverse end edges, wherein each of said colored regions has a colored region area that is more than about 1% of said main body portion area and the sum of said colored region areas is more than about 6% of said main body portion area.

5. The absorbent article according to claim 1, wherein said focal region is symmetrical about said longitudinal centerline.

6. The absorbent article according to claim 1, wherein said absorbent article has two spaced apart longitudinal side edges, and two spaced apart transverse end edges, wherein said absorbent article has a main body portion defined by said two spaced apart longitudinal side edges and said two spaced apart transverse end edges, wherein said main body portion has a main body portion area bounded by said longitudinal side edges and said transverse end edges, wherein said focal region has a focal region area, wherein said focal region area is less than about 3% of said main body portion area.

7. The absorbent article according to claim 1, wherein at least two of said colored regions are disposed on opposing sides of a line parallel to said transverse centerline and at least two of said colored regions are disposed on opposing sides of said longitudinal centerline.

8. The absorbent article according to claim 1, wherein said focal region is a point.

9. The absorbent article according to claim 1, wherein said focal region is on said transverse centerline.

10. The absorbent article according to claim 1, wherein the difference in color, as measured on the viewing surface of said absorbent article, between a colored region and a portion of said absorbent article outside of a colored region is calculated using the L, a, and b values by the formula $\Delta E=[(L^*_X - L^*_Y)^2 + (a^*_X - a^*_Y)^2 + (b^*_X - b^*_Y)^2]^{1/2}$, wherein the difference in color between a colored region and a portion of said absorbent article outside of a colored region is at least about 3.5.

11. The absorbent article according to claim 1, wherein the difference in color, as measured on the viewing surface of said absorbent article, between a colored region and a portion of said absorbent article outside of a colored region is calculated using the L, a, and b values by the formula $\Delta E=[(L^*_X - L^*_Y)^2 + (a^*_X - a^*_Y)^2 + (b^*_X - b^*_Y)^2]^{1/2}$, wherein the difference in color between a colored region and a portion of said absorbent article outside of a colored region is at least about 6.

12. The absorbent article according to claim 1, wherein said absorbent article comprises an absorbent core in a facing relationship with said topsheet, wherein said colored regions are part of said absorbent core.

13. The absorbent article according to claim 1, wherein said colored regions are part of said topsheet.

14. The absorbent article according to claim 1, wherein said absorbent article comprises an absorbent core in a facing relationship with said topsheet, wherein said colored regions are part of an insert between said topsheet and said absorbent core.

15. The absorbent article according to claim 1, wherein said colored regions are part of said bottom surface of said topsheet.

16. The absorbent article according to claim 1, wherein said colored regions comprise a plurality of closely spaced graphic elements.

17. An absorbent article comprising a compressed absorbent member having an insertion end, a withdrawal end, a longitudinal axis, a circumferential surface about said longitudinal axis, the absorbent article comprising an exterior surface, said exterior surface being a viewing surface;

at least three colored regions, said colored regions being viewable from said viewing surface of said absorbent article, each said colored region having a periphery wherein none of said colored regions lie entirely within a periphery of another colored region;

wherein each said colored region has a longest dimension and a major axis, said longest dimension defined by the maximum straight-line distance between two points on said periphery, said major axis extending between and beyond two points on said periphery separated by said longest dimension, wherein said colored regions are spaced apart from one another and are provided in a region fully within the maximum lateral extent of the absorbent core;

wherein each said colored region has an aspect ratio greater than about one;

said major axis of each said colored region converging towards a common focal region on said viewing surface, said major axis of each of said colored regions being oriented about said focal region and extending toward an edge of said absorbent article.

18. The absorbent article according to claim 17, wherein said circumferential surface has a circumferential surface area, wherein each of said colored regions has a colored region area that is more than about 1% of said circumferential surface area and the sum of said colored region areas is more than about 6% of said circumferential surface area.

19. The absorbent article according to claim 17, wherein the difference in color, as measured on the viewing surface of said absorbent article, between a colored region and a portion of said absorbent article outside of a colored region is calculated using the L, a, and b values by the formula $\Delta E=[(L^*_X-L^*_Y)^2+(a^*_X-a^*_Y)^2+(b^*_X-b^*_Y)^2]^{1/2}$ and wherein the difference in color between a colored region and a portion of said absorbent article outside of a colored region is at least about 3.5.

20. The absorbent article according to claim 17, wherein said absorbent article further comprises an overwrap substantially covering said circumferential surface, said overwrap having an inner facing surface and an outer facing surface opposing said inner facing surface, said inner facing surface oriented towards said absorbent member and said outer facing surface being the viewing surface.

* * * * *